(12) United States Patent
Sah (10) Patent No.: US 11,058,433 B2
(45) Date of Patent: Jul. 13, 2021

(54) KNEE SURGERY GUIDE AND METHOD

(71) Applicant: Alexander Sah, Fremont, CA (US)

(72) Inventor: Alexander Sah, Fremont, CA (US)

(*) Notice: Subject to any disclaimer, the term of this patent is extended or adjusted under 35 U.S.C. 154(b) by 99 days.

(21) Appl. No.: 16/197,116

(22) Filed: Nov. 20, 2018

(65) Prior Publication Data

US 2019/0183514 A1 Jun. 20, 2019

Related U.S. Application Data

(63) Continuation of application No. 15/846,023, filed on Dec. 18, 2017, now Pat. No. 10,159,494.

(51) Int. Cl.
| | | |
|---|---|---|
| *A61B 17/15* | (2006.01) | |
| *A61B 17/17* | (2006.01) | |
| *A61B 17/16* | (2006.01) | |

(52) U.S. Cl.
CPC .......... *A61B 17/155* (2013.01); *A61B 17/157* (2013.01); *A61B 17/1764* (2013.01); *A61B 2017/1602* (2013.01)

(58) Field of Classification Search
CPC .. A61B 17/155; A61B 17/154; A61B 17/1764
See application file for complete search history.

(56) References Cited

U.S. PATENT DOCUMENTS

| | | |
|---|---|---|
| 5,417,694 A | 5/1995 | Marik et al. |
| 5,569,260 A | 10/1996 | Petersen |
| 5,709,689 A | 1/1998 | Ferrante et al. |
| 6,258,096 B1 | 7/2001 | Seki |
| 6,916,341 B2 | 7/2005 | Rolston |
| 7,887,542 B2 * | 2/2011 | Metzger ............... A61B 17/157 606/87 |
| 8,167,888 B2 | 5/2012 | Steffensmeier |
| 8,828,012 B2 | 9/2014 | May et al. |
| 8,828,016 B2 | 9/2014 | Major et al. |
| 10,159,494 B1 | 12/2018 | Sah |
| 2003/0225413 A1 | 12/2003 | Sanford et al. |
| 2004/0102785 A1 | 5/2004 | Hodorek et al. |
| 2006/0036257 A1 | 2/2006 | Steffensmeier |
| 2010/0222783 A1 | 9/2010 | May et al. |
| 2016/0199077 A1 | 7/2016 | Dungy |
| 2017/0100132 A1 | 4/2017 | Collazo |
| 2017/0319216 A1 | 11/2017 | Harris |

OTHER PUBLICATIONS

International Search Report and Written Opinion for International Application No. PCT/US2018/066289, dated Apr. 1, 2019.

(Continued)

*Primary Examiner* — Andrew Yang
(74) *Attorney, Agent, or Firm* — Wolf, Greenfield & Sacks, P.C.

(57) ABSTRACT

Method and apparatus for performing an anterior distal femoral resection. A distal femoral resection is formed and used as a surface from which to base an anterior distal femoral resection cutting guide apparatus. The cutting guide apparatus may include a position block and an attached cutting guide. The position block is placed against the anterior distal femoral resection, and the orientation of the anterior cutting guide is set, at least in part, based on the anterior distal femoral resection.

6 Claims, 12 Drawing Sheets

(56) References Cited

OTHER PUBLICATIONS

PCT/US2018/066289, Apr. 1, 2019, International Search Report and Written Opinion.
[No Author Listed] iDuo® G2 Surgical Technique Guide: Patient-Specific Biocompartmental Knee Resurfacing System. ConforMIS, Inc. 2012, 24 pages.
[No Author Listed] Persona: The Personalized Knee System Surgical Technique. Zimmer, Inc. 2015, 72 pages.
[No Author Listed] Surgical Technique: Journey PFJ, Patellofemoral Joint with Oxidized Zirconium. Smith & Nephew, Inc. 28 pages [publicly available prior to Dec. 18, 2017].
[No Author Listed] Zimmer® Gender Solutions™ Patello-Femoral Joint (PFJ) System Surgical Technique. Zimmer, Inc. 2008, 38 pages.
[No Author Listed] Zimmer® Unicompartmental High Flex Knee: Spacer Block Surgical Technique. Zimmer, Inc. 2011, 32 pages.
Rolston et al., Biocompartmental Knee Arthroplasty: A Bone-Sparing, Ligament-Sparing, and Minimally Invasive Alternative for Active Patients. Healio. https://www.healio.com/orthopedics/knee/news/online/%7bc83433ee-c0bb-4d9c-bc9e-99a1f4a0814c%7d/bicompartmental-knee-arthroplasty-a-bone-sparing-ligament-sparing-and-minimally-invasive-alternative-for-active-patients, Aug. 1, 2007, 7 pages.

\* cited by examiner

KNEE SURGERY GUIDE AND METHOD

RELATED APPLICATIONS

This Application is a Continuation of U.S. application Ser. No. 15/846,023, filed Dec. 18, 2017, and entitled "KNEE SURGERY GUIDE AND METHOD," which is incorporated by reference herein in its entirety.

FIELD

This application relates generally to knee surgery guides and methods, and more specifically to devices and methods for performing anterior distal femoral resections.

DESCRIPTION OF THE RELATED ART

Patellofemoral partial knee replacement surgeries typically include an anterior distal femoral resection. The coronal resection forms a plane which is parallel to an anatomic longitudinal axis of the femur. To form the resection, a slotted cutting guide is attached to the femur, and an oscillating saw is inserted through the slot to cut the anterior portion of the femur. To properly orient the cutting guide, one of two methods is typically used.

In a first method, a rod is inserted into the medullary canal, and a guide is attached to the rod. The canal is oriented in the same direction as the longitudinal axis of the femur, and therefore the cutting guide can be oriented to form a parallel resection.

In a second method, a custom cutting guide may be prepared based on CT or MRI and/or other types of imaging. The guide is attachable to the femur with pins or screws. By knowing the specific shape of the femur, the guide is formed such that when attached, the guide is oriented to form a planar cut parallel to the femur longitudinal axis.

SUMMARY

Embodiments disclosed herein take an inherently different approach to positioning a cutting guide to form an anterior distal femoral resection. In some embodiments, the medullary canal is not violated and no custom guide device is required. As such, according to some embodiments, pre-operative imaging scans are not required, and the risks associated with intra-medullary rods are avoided.

According to one embodiment, a method of performing an anterior distal femoral resection on a femur using a cutting guide apparatus is provided. The method includes performing a proximal tibial resection to form a proximal tibial resection surface, and performing an extramedullary distal femoral resection to form a distal femoral resection surface parallel to the proximal tibial resection surface, the distal femoral resection being performed by using a spacer block that is placed against the proximal tibial resection surface. The method further includes placing a position block against the distal femoral resection surface, and performing a distal femoral anterior resection using an anterior cutting guide that is attached to the position block.

According to another embodiment, a method of performing an anterior distal femoral resection on a femur using a cutting guide apparatus is provided. The method includes performing an extramedullary distal femoral resection to form a distal femoral resection surface, placing a position block against no more than one condyle of the distal femoral resection surface, and performing a distal femoral anterior resection using an anterior femoral cutting guide that is attached to the position block.

According to a further embodiment, an apparatus for guiding an anterior distal femoral resection includes a position block having a contact surface configured to be contacted to no more than one condyle of a distal femur resection surface, and an anterior femoral cutting guide attached to the position block.

According to yet another embodiment, an apparatus for guiding an anterior distal femoral resection includes a position block having a planar contact surface configured to be contacted to a distal femoral resection surface, and an anterior femoral cutting guide attached to the position block, the cutting guide having a cutting slot. An anterior/posterior height of the cutting slot is adjustable relative to the position block.

According to a further embodiment, a method of performing an anterior distal femoral resection on a femur using a cutting guide apparatus is provided. The method includes performing a proximal tibial resection to form a proximal tibial resection surface, and performing an extramedullary distal femoral resection to form a distal femoral resection surface parallel to the proximal to the proximal tibial resection surface, the distal femoral resection being performed by using a spacer block that is placed against the proximal tibial resection surface. The method further comprises placing a position block against the proximal tibial resection surface, and performing a distal femoral anterior resection using an anterior cutting guide that is attached to the position block.

According to another embodiment, an apparatus for spacing a trochlear cutting guide from a distal femoral resection surface is provided. The apparatus includes a movable arm attached to a distal femoral resection surface on a medial condyle, with the arm being configured to reach an anterior distal femoral resection surface. The apparatus also includes a curved end piece attached at an end of the arm.

According to a further embodiment, a method of spacing a trochlear cutting guide from a distal femoral resection surface on a medial condyle is provided. The method includes attaching an arm to a distal femoral resection surface on a medial condyle and directing an end of the arm toward an anterior distal femoral resection surface. The method also includes placing a trochlear cutting guide on an anterior distal femoral resection surface such that the trochlear cutting guide contacts the end of the arm or is spaced from the end of the arm.

DETAILED DESCRIPTION

Embodiments disclosed herein permit the performance of an extramedullary distal anterior femoral resection. An important aspect of such an anterior resection is to form a resection surface that is oriented at a desired angle relative to the sagittal plane of the femur. In many cases, it is desired to have the resection surface be parallel to the femoral axis in the sagittal plane. As discussed above, achieving a desired orientation typically requires pre-operative scans or the use of an intra-medullary rod.

According the present disclosure, a cutting guide is oriented relative to a femur by using a previously-formed distal femoral resection that is perpendicular to the femur's longitudinal axis. For example, according to one method, the tibia is cut to form a proximal tibial resection having a resection surface which is perpendicular to the longitudinal axis of the femur. A spacer block with an attached cutting guide then is placed against the tibial resection surface and a distal femoral resection is performed on a condyle. A position block is then placed against the distal femoral resection surface, and a cutting guide is mounted to the femur using the position block. Because the distal femoral resection surface is perpendicular to the femur longitudinal axis, the cutting guide can be oriented at a desired orientation relative to the femur longitudinal axis.

By using such an approach, the medullary canal may not be violated and a cutting guide customized according to pre-operative scans may not be required.

In some embodiments, the guide permits adjustment of the anterior/posterior height of the cutting guide. The rotation of the guide about an axis that is parallel to the femur longitudinal axis is also adjustable in some embodiments.

The position block used to mount the anterior cutting guide may be the spacer block used as part of the distal femoral resection cut. In other embodiments, the position block may be a position block specifically adapted to be used with the anterior cutting guide, and such a position block may be attached to the femur after the distal femoral resection cutting guide has been removed. In still further embodiments, the position block may be a posterior chamfer cutting guide, and the anterior cutting guide may be attached to the posterior chamfer cutting guide.

According to one aspect of the present disclosure, the performance of a patellofemoral partial knee replacement may be combined with the performance of a medial partial knee replacement. A medial partial knee replacement may employ the use of a tibial cut and corresponding distal femoral resection to form a planar surface on the distal end of the femur with the planar surface being perpendicular to the femur longitudinal axis. A device according to the present disclosure may be mounted to this planar surface as part of orienting the anterior cutting guide.

Figure 1:
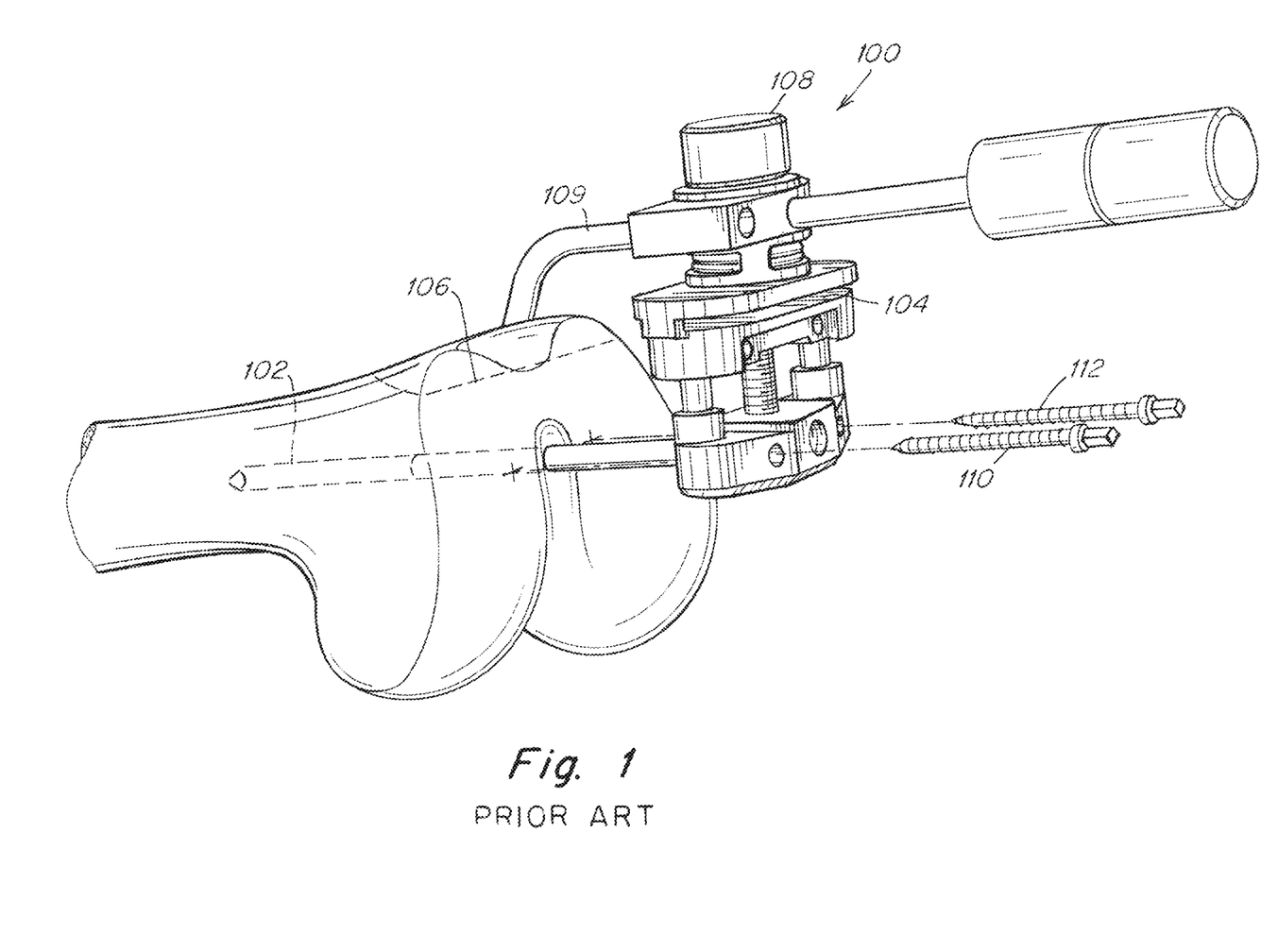
FIG. 1 shows a prior art cutting guide attached to an intra-medullary rod.
Figure 2:
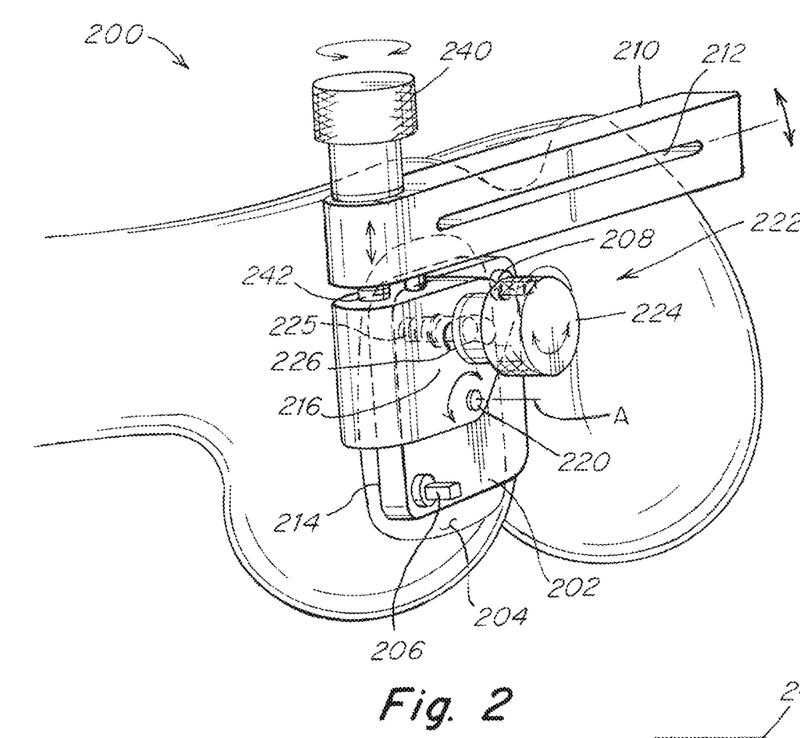
FIG. 2 is a perspective view of an anterior distal femoral resection cutting guide apparatus attached to a distal end of a femur according to one aspect of the present disclosure.
Figure 3:
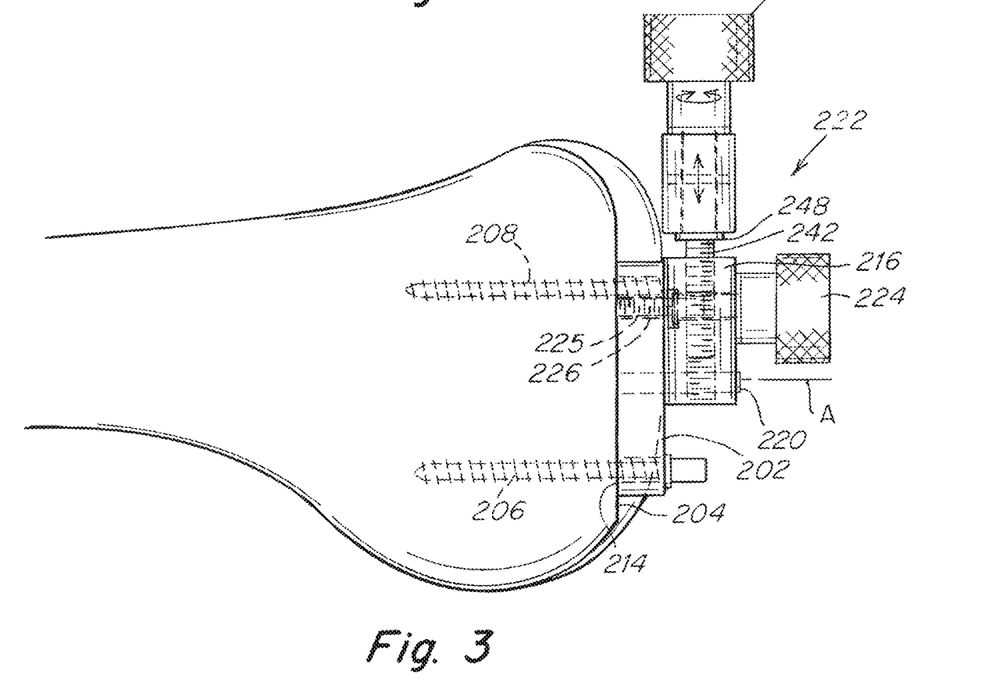
FIG. 3 is a side view of the apparatus of FIG. 2.
Figure 4:
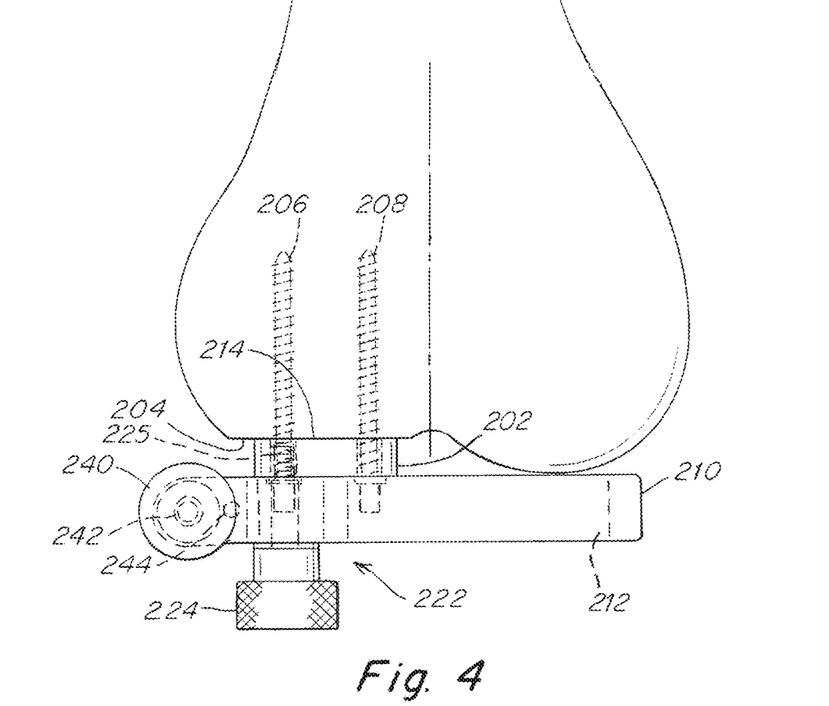
FIG. 4 is an top view of the apparatus of FIG. 2.
Figure 5:
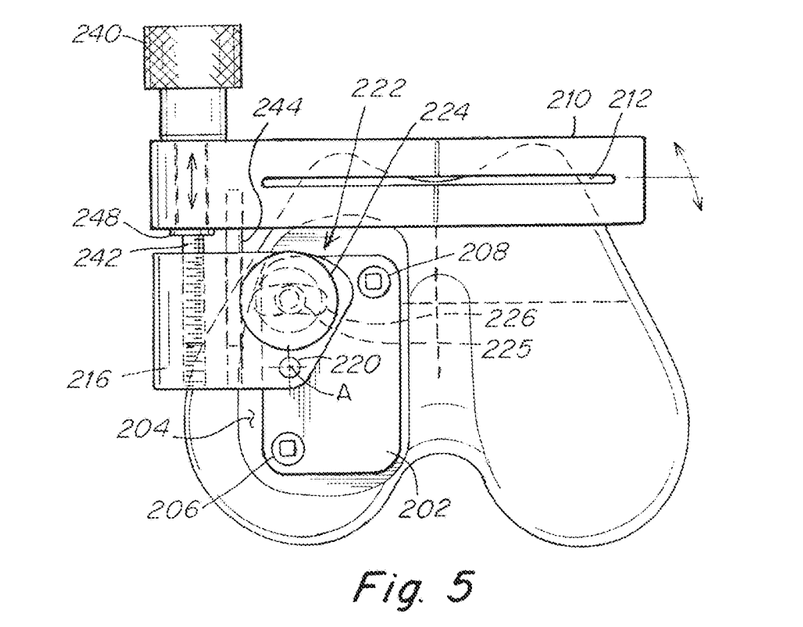
FIG. 5 is an end view of the apparatus of FIG. 2.
Figure 6:
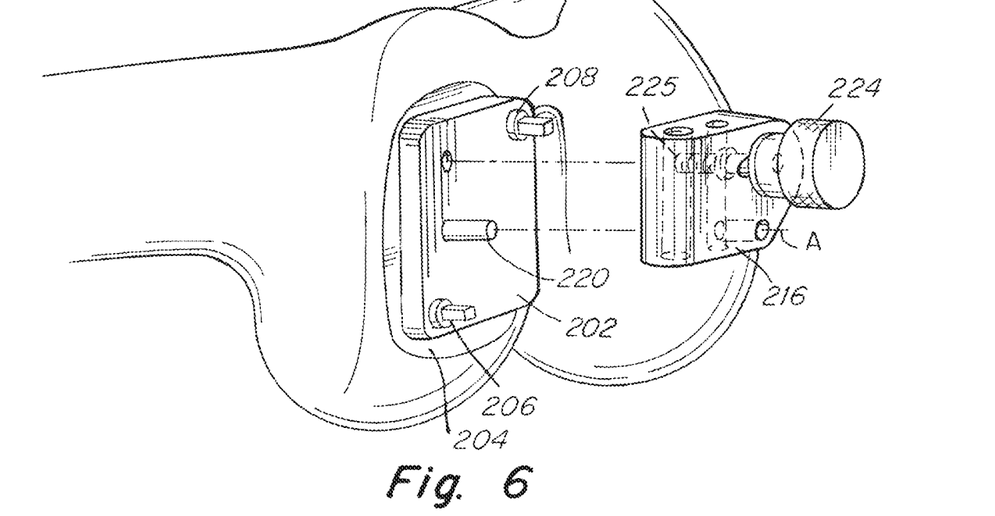
FIG. 6 is a perspective view of a portion of the apparatus of FIG. 2 with a portion exploded for ease of illustration.

Turning to the figures, FIG. 1 shows a prior art anterior cutting guide arrangement wherein a cutting guide 100 is attached to an intermedullary rod 102. A slot 104 is oriented to cut a planar surface along a cut line 106. The anterior/posterior height of the cut is adjustable using a thumb screw 108, and is adjusted until a telescoping boom 109 contacts the cortex. Once the intermedullary rod 102 is fully inserted into the medullary canal, two screws 110, 112 are used to secure the guide to the femur.

FIGS. 2-6 shows an anterior femoral cutting guide arrangement 200 according to one embodiment of the present disclosure where the use of an intermedullary rod is avoided. A spacer block 202 is positioned against a distal femoral resection surface 204 using two screws 206, 208, or any other suitable attachment arrangement. A cutting guide 210 includes a slot 212 through which an oscillating saw or other cutting device may be placed. In some embodiments, the cutting guide 210 may include a structure other than a slot to guide a cutting device.

The spacer block 202 may be adapted to attach to only a single condyle of the femur in some embodiments. For example, in the embodiment illustrated in FIGS. 2-6, spacer block 202 is attached to a medial condyle of the femur. Spacer block 202 may have a planar surface 214 arranged to be placed against a planar distal femoral resection surface. By linking the cutting guide orientation to the distal femoral resection surface, the orientation of the resulting anterior resection surface relative to the femur longitudinal axis may be controlled. In many embodiments, it is desirable to have the surface be parallel to the longitudinal axis.

A rotating block 216 may be employed to permit rotation of cutting guide slot 212 about an axis A that is parallel to the femur longitudinal axis. In some embodiments, rotating block 216 pivots relative to spacer block 202 via a pivot joint 220. Once the rotating block 216 has been pivoted to a desired rotation, the rotating block may be secured with a locking arrangement 222. The locking arrangement 222 may include a clamping knob 224 attached to a bolt 225. Rotating the clamping knob 224 presses the clamping knob against the rotating block, which in turn presses against spacer block 202 to secure the angle of the rotating block. The rotating block includes a curved slot 226 to permit the rotational adjustment of the rotating block when the clamping knob is loosened. A spring clip 227 may be attached to bolt 225 to hold the clamping knob 224 and the bolt 225 to rotating block 216.

Figure 7:
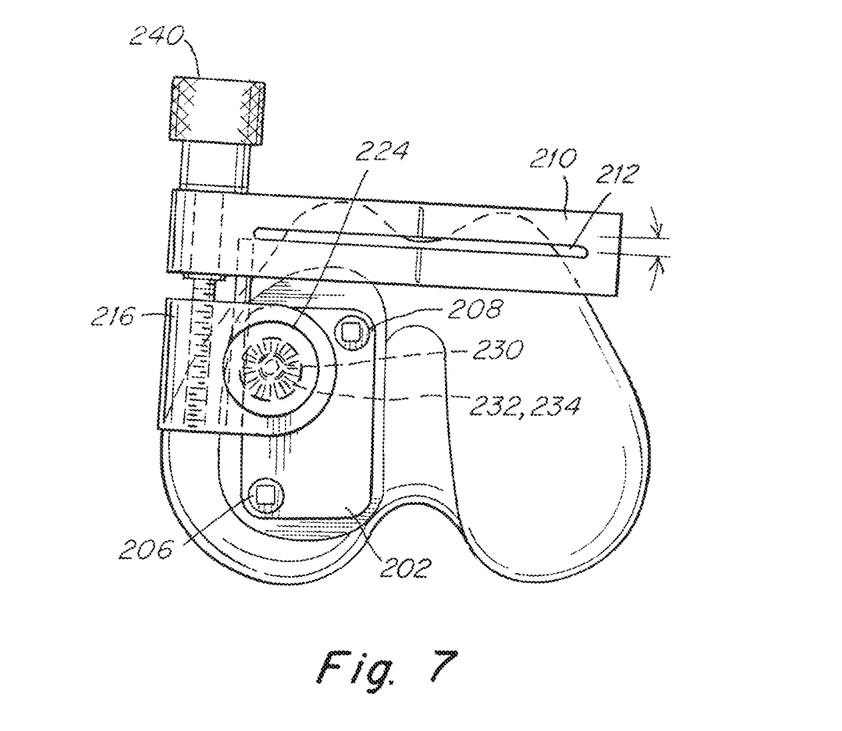
FIG. 7 is an end view of an alternative arrangement for permitting rotation and locking of a rotating block relative to a spacer block according to one embodiment.
Figure 8:
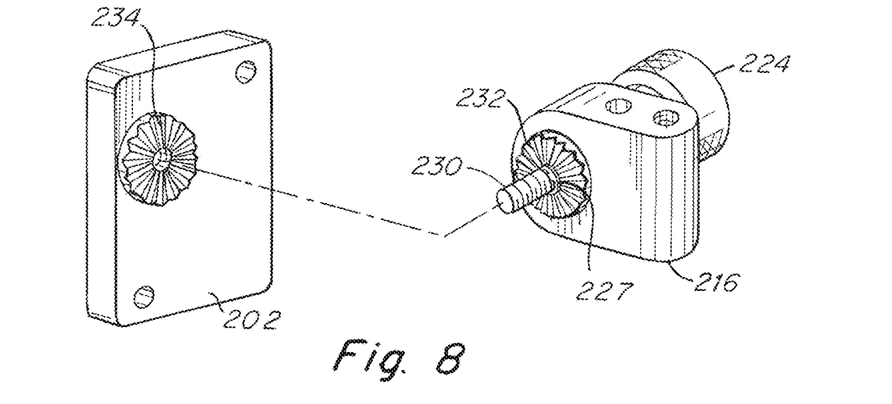
FIG. 8 is an exploded perspective view of the clamping arrangement of the embodiment of FIG. 7.

In other embodiments, the pivot joint may include a screw arrangement wherein once the desired rotation is achieved, the screw can be tightened to secure the rotation. For example, as shown in the embodiment of FIGS. 7-8, clamping knob 224 may be attached to a bolt 230 which acts both as part of the clamping arrangement and the axis about which the rotating block pivots. Once the desired rotation is reached, the claiming knob is tightened to press a first, rotating block clamping surface 232 against a second, spacer block clamping surface 234.

Any suitable arrangement for setting the rotation angle may be used, and the described embodiments are presented as examples only. In some embodiments, the cutting guide arrangement may not include the rotating block, and may not include the capability of rotation about an angle parallel to the femur longitudinal axis.

An anterior/posterior height of the cutting guide 210, and in particular the cutting guide slot 212, may be adjusted using a thumb screw 240 which rotates a bolt 242 into and out of rotating block 216. A guide rod 244 simultaneously moves into and out of rotating block 216, and the guide rod restricts or prevents distal/proximal rotation of the cutting guide when the thumb screw is being rotated. In some embodiments, an end of the cutting guide is captured between the thumb screw 240 and a flange 248.

Figure 9:
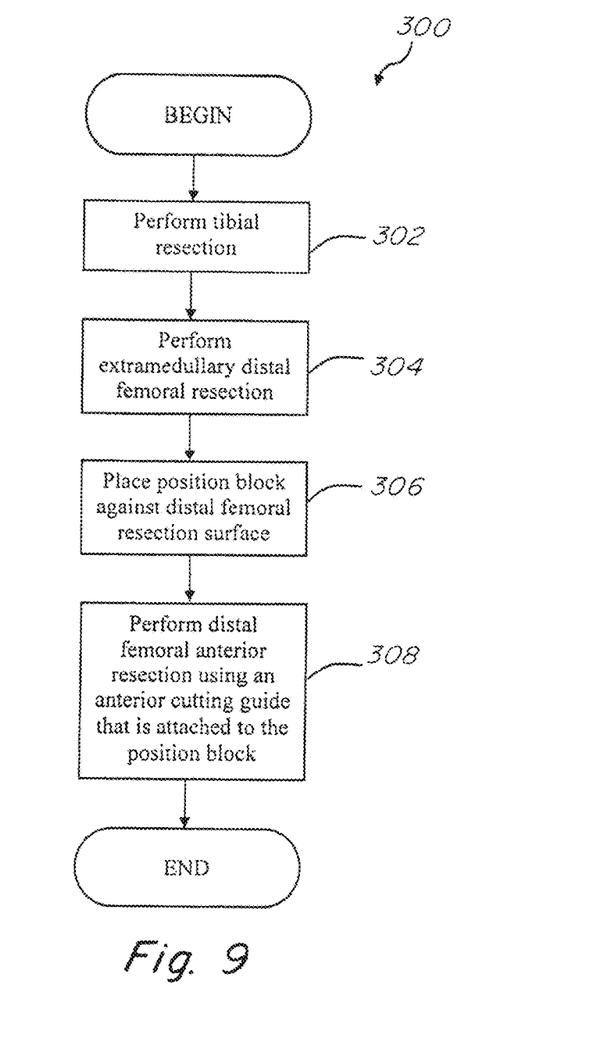
FIG. 9 is a flowchart of a method of performing an anterior distal femoral resection according to one embodiment of the present disclosure.

FIG. 9 is a flowchart of a method 300 of performing an anterior distal femoral resection according to one embodiment of the present disclosure. In a first act 302, a tibial resection is performed. An extramedullary distal femoral resection is then performed in an act 304. Act 304 may be performed using a cutting guide employing a spacer block positioned against the tibial resection with the leg in an extended position. In an act 306, a position block is placed against the distal femoral resection surface. A distal femoral anterior resection is then performed in an act 308 by using an anterior cutting guide attached to the position block that is positioned against the distal femoral resection surface.

Figure 10:
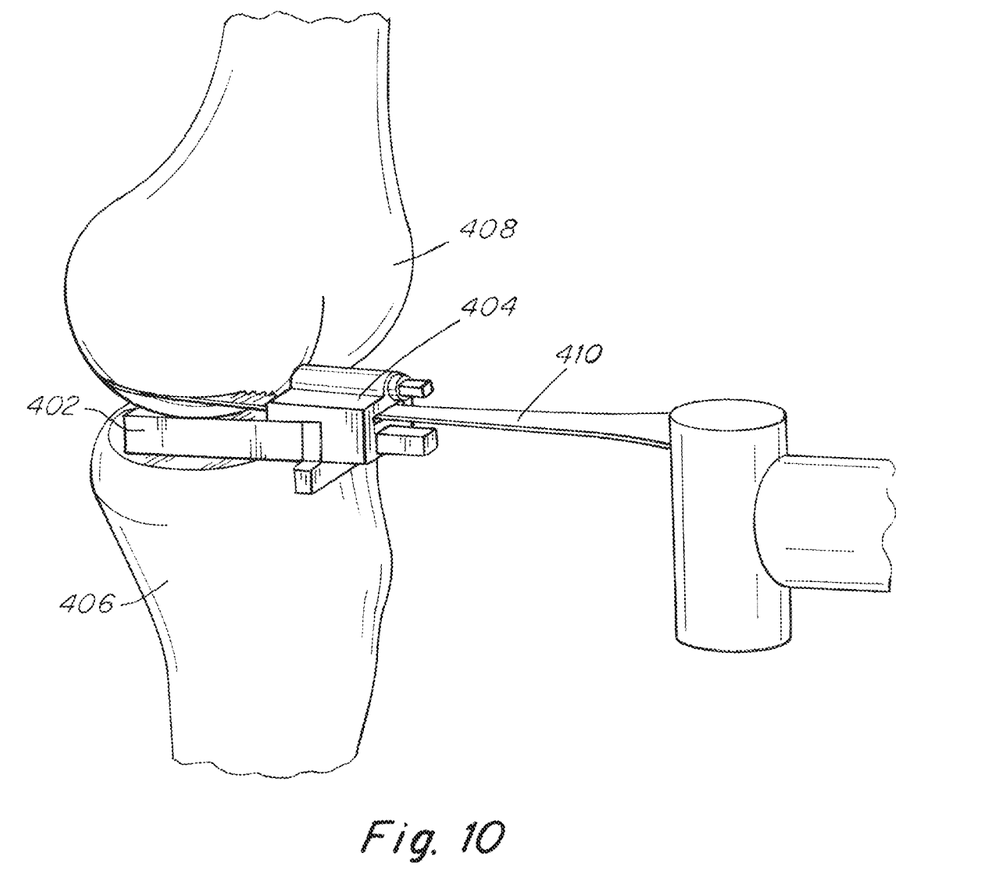
FIG. 10 shows a spacer block and cutting guide positioned between a tibia and a femur.

The positioning of a cutting guide to perform act 304 is illustrated in FIG. 10 according to one embodiment. A spacer block 402 and a cutting guide 404 are positioned between a tibia 406 and a femur 408 with the leg in an extended position. A oscillating saw 410 is inserted through a slot in cutting guide 404 to form the distal femoral resection surface.

Once the distal femoral resection surface is formed, cutting guide arrangement 200 may be attached to the femur as described above with reference to FIGS. 2-6.

Figure 11:
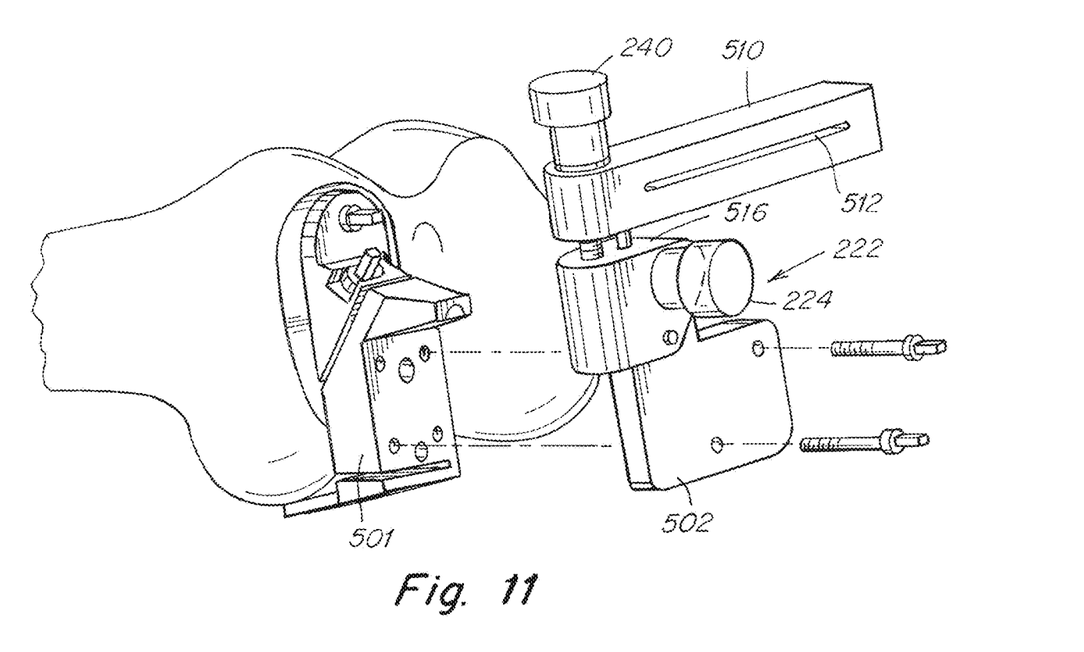
FIG. 11 is a perspective view of a cutting guide that is attachable to a posterior chamfer cut guide according to one embodiment.
Figure 12:
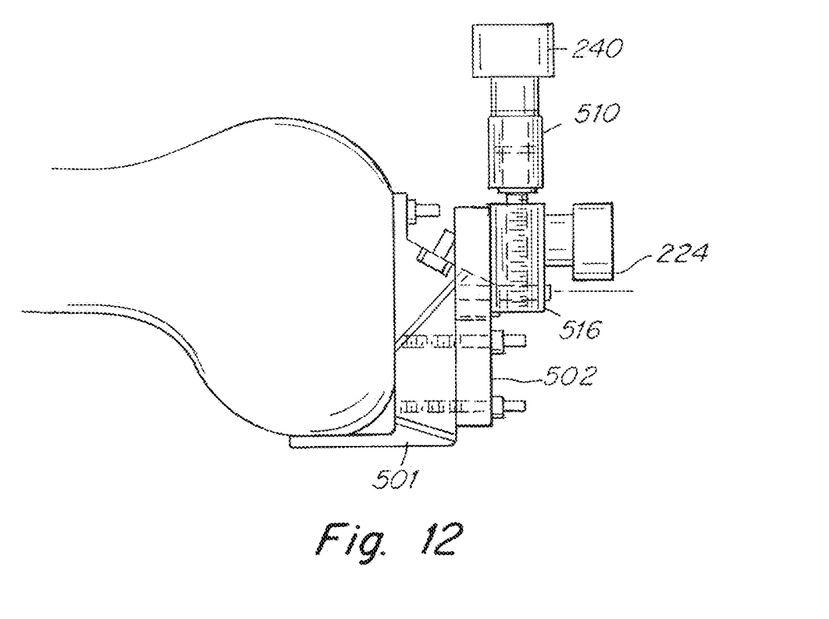
FIG. 12 is a side view of the embodiment of FIG. 11 with the cutting guide attached to the posterior chamfer cut guide.

In alternative embodiments, instead of using one of the position blocks 202 shown in FIGS. 2-6, a posterior chamfer cut guide may be used as a position block to which an anterior cutting guide may be attached. For example, as shown in FIGS. 11 and 12, a rotating block 516 may be attached to a position block 202, which in turn is attached to a posterior chamfer cut guide 501. A cutting guide 510 with a slot 512 is connected to the rotating block 516.

With such an arrangement, the performance of a medial partial knee replacement can be combined with a patellofemoral partial knee replacement, and the posterior chamfer cut guide 501 may be used not only to cut a chamfer surface, but also as a position block for an anterior cutting guide. In some embodiments, the anterior cutting guide 510 is removably attachable to the posterior chamfer cut guide 501 such that a chamfer cut may be made without the anterior cutting guide attached.

Figure 18:
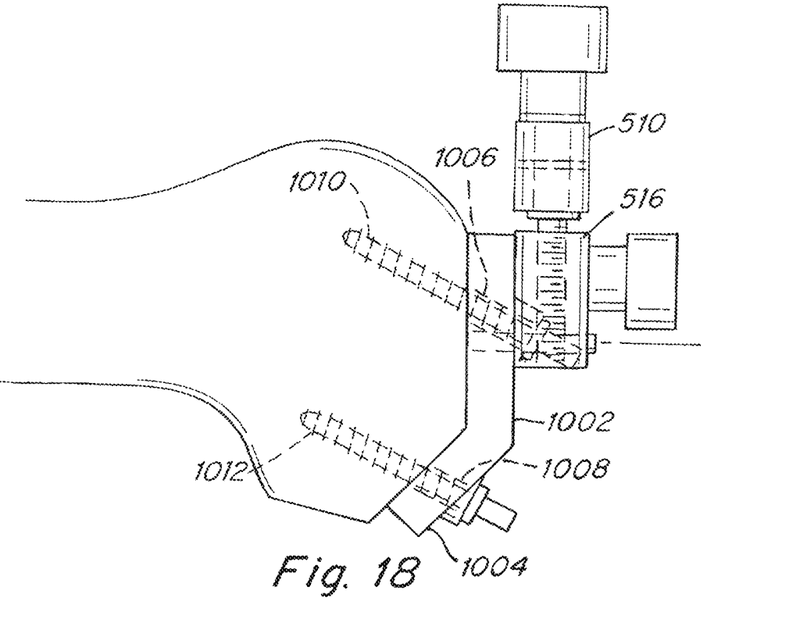
FIG. 18 is a side view of an anterior distal femoral resection cutting guide apparatus attached to a distal end of a femur according to one aspect of the present disclosure.

As shown in FIG. 18, in another alternative embodiment, a position block 1002 for the anterior cutting guide may be attached to the femur via position holes which were previously used to hold a posterior chamfer cut guide. In such an arrangement, after the distal femoral resection surfaces is formed, position holes are drilled and a posterior chamfer cut guide is attached to the distal planar surface. A posterior chamfer cut is made, resulting in a planar surface 1004, and the posterior chamfer cut guide is then removed. The position block 1002 of the anterior cutting guide may have holes 1006, 1008 that align with the previously drilled position holes 1010, 1012 in the femur, and screws may be inserted through the anterior cutting guide position block and into the position holes. Connectors other than screws may be used, such as rods. With the anterior cutting guide device attached to the planar face of the condyle, the cutting guide slot orientation is known and may be used to perform a distal femoral anterior resection.

Figure 13:
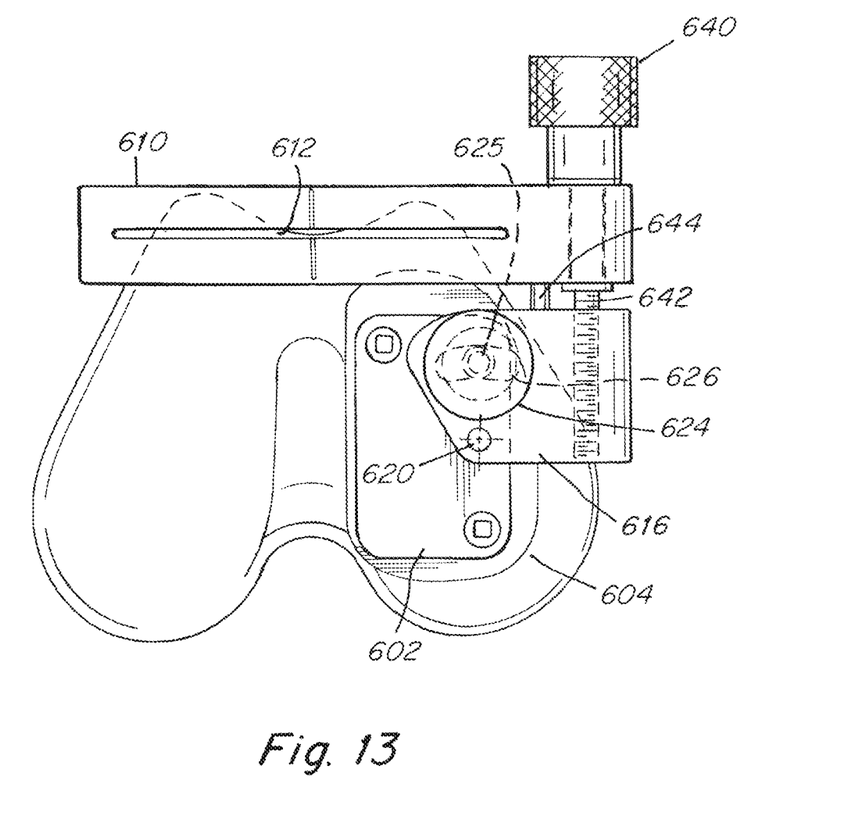
FIG. 13 shows a position block attached to a lateral condyle.

The anterior cutting guide arrangement may be attached to the lateral condyle of the femur in some embodiments. For example, as shown in FIG. 13, a position block 602 is attached to the lateral condyle 604. A rotating block 616 and an anterior cutting guide arrangement 610 similar to the rotating block 216 and the anterior cutting guide arrangement 210 shown in FIGS. 2-6 may be attached to position block 602. The cutting guide and rotating block attached to the lateral condyle may have a reverse arrangement as compared to the arrangement attached to the medial condyle.

A rotating block 616 pivots relative to position block 602 via a pivot joint 620. Once the rotating block 616 has been pivoted to a desired rotation, the rotating block may be secured with a locking arrangement. The locking arrangement may include a clamping knob 624 attached to a bolt 625. Rotating the clamping knob 624 presses the clamping knob against the rotating block, which in turn presses against position block 602 to secure the angle of the rotating block. The rotating block includes a curved slot 626 to permit the rotational adjustment of the rotating block when the clamping knob is loosened.

To provide height adjustability, a thumbscrew 640 rotates a bolt 642 into and out of rotating block 616. A guide rod 644 simultaneously moves into and out of rotating block 616, and the guide rod restricts or prevents distal/proximal rotation of the cutting guide when the thumb screw is being rotated.

Figure 14:
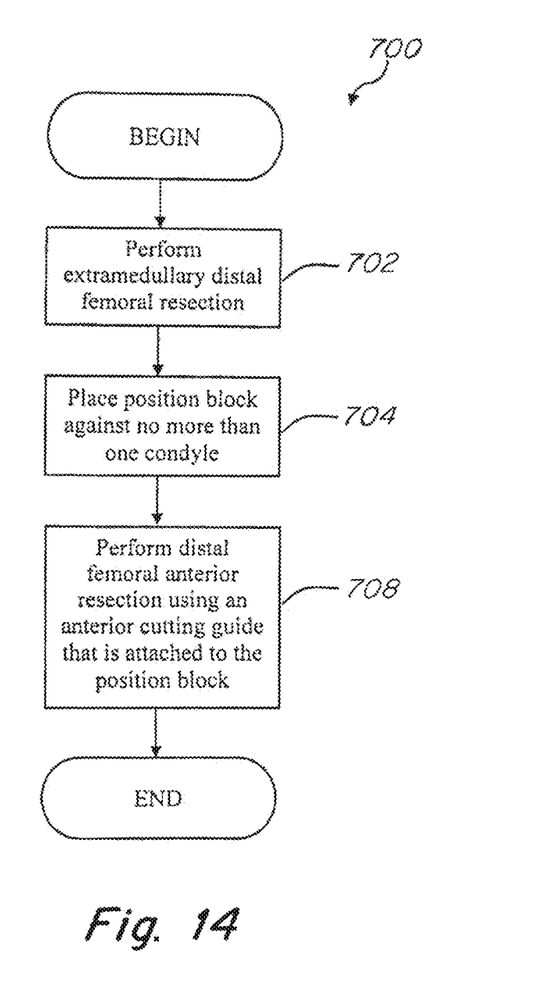
FIG. 14 is a flowchart of a method of performing an anterior distal femoral resection according to one embodiment of the present disclosure.

According to one aspect of the present disclosure, one or more of the devices disclosed herein may be used to perform a distal femoral anterior resection while using a position block that is placed against no more than one condyle of the distal femoral resection surface. For example, a method 700 is shown in FIG. 14.

In an act 702, an extramedullary distal femoral resection is performed to form a distal femoral resection surface. A position block is placed against no more than one condyle of the distal femoral resection surface in an act 704. In an act 706, a distal femoral anterior resection is performed using an anterior femoral cutting guide that is attached to the position block.

When performing method 700, the position block may be a position block specifically designed for use with an anterior cutting guide. In alternative embodiments, the position block may be a posterior chamfer cutting guide, and have an anterior cutting guide attached thereto.

Figure 15:
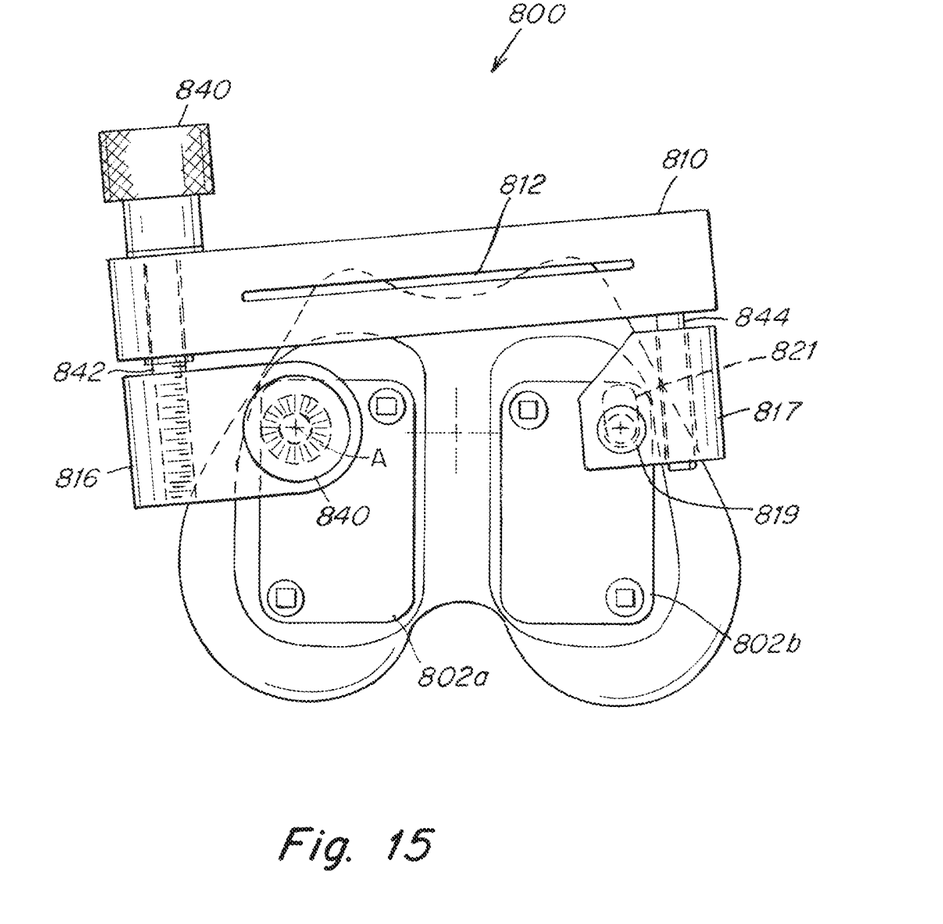
FIG. 15 shows a cutting guide apparatus attached to both condyles, the cutting guide having an adjustable anterior/posterior height.

An anterior cutting guide device may be attached to both condyles in some embodiments, and include anterior/posterior height adjustment of the cutting slot. By way of illustration, FIG. 15 shows an anterior cutting guide apparatus 800 including two spacer blocks 802a, 802b attached to both condyles of a distal femoral resection. A cutting guide 810 with a cutting guide slot 812 is mounted to a rotating block 816, which in turns rotates about axis A relative to spacer block 802a. As such, the cutting guide slot 812 is rotatable about the anatomic longitudinal axis of the femur or an axis parallel to the longitudinal axis of the femur to adjust the tilt of the cutting guide slot 812.

The anterior/posterior height of the cutting guide slot is adjustable by rotating a bolt 842 with a thumbscrew 840. A sliding block 817 may be positioned on the opposite condyle by way of attachment to position block 802b. A guide post 844 restricts or prevents rotation of the cutting guide 810 in the distal/proximal direction. The sliding block 817 may include a short pin 819 which slides within a curved slot 821 in position block 802b to allow sliding block 817 to move when rotating block 816 is rotated.

Figure 16:
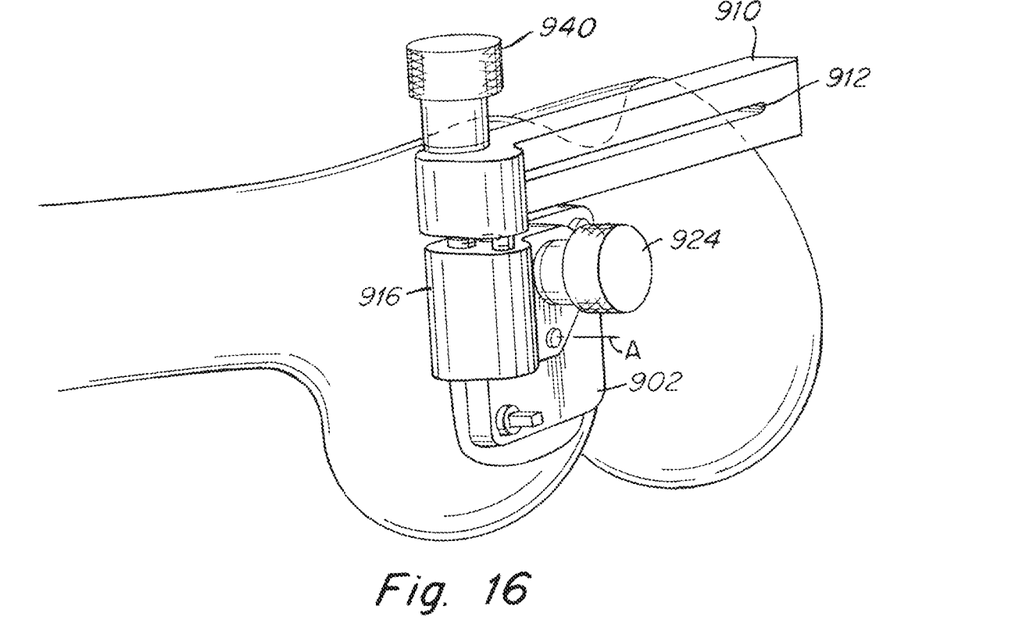
FIG. 16 is a perspective view of an anterior distal femoral resection cutting guide apparatus that is positionable at the distal end of the femur or at the medial side of the femur.
Figure 17:
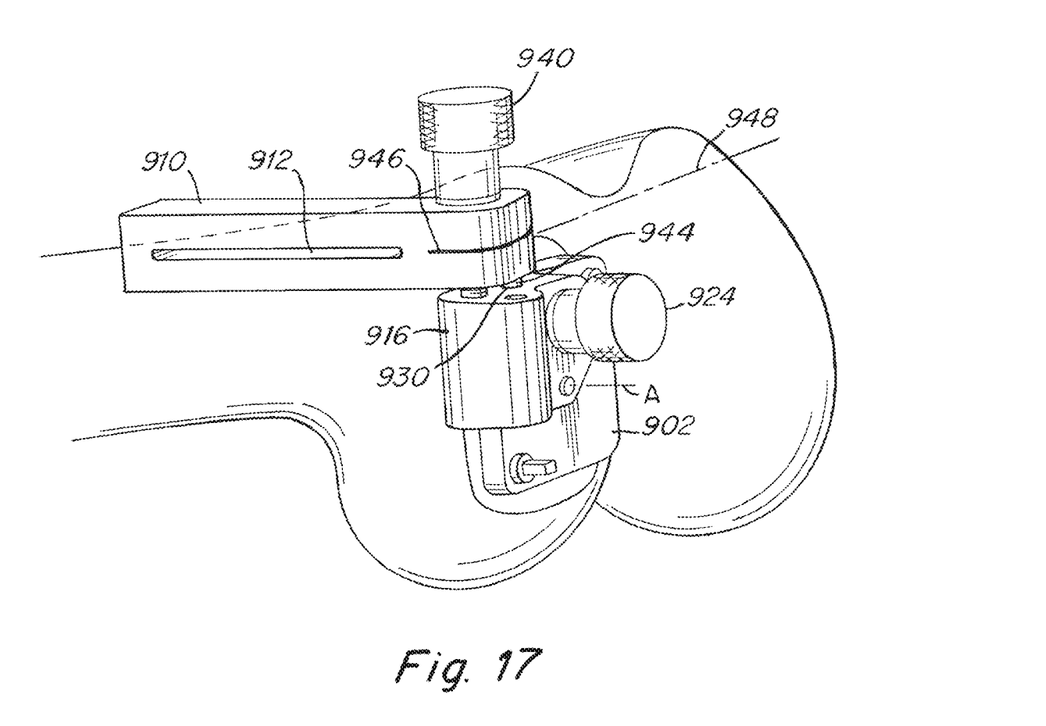
FIG. 17 shows the cutting guide of FIG. 16 positioned at the medial side of the femur.

FIGS. 16-17 show an alternative embodiment where an anterior femoral cutting guide arrangement 900 includes a cutting guide 910 which is positionable either in an orientation similar to other embodiments disclosed herein (FIG. 16) or in an orientation along a medial side of the femur (FIG. 17). Similar to other embodiments, the arrangement may include a thumbscrew 940 for height adjustment, a clamping knob 924, a position block 902, and a rotating block 916 that rotates about an axis A. Different from other embodiments disclosed herein, rotating block 916 includes a second guide rod slot 930 to receive a guide rod 944. As shown in FIG. 17, the cutting guide 910 may be rotated ninety degrees such that guide rod 944 is received in second guide rod slot 930 and the cutting guide 910 is positioned along a medial side of the femur. A guide line 946 may be included to aid in determining whether cutting guide 910 is in a correct orientation, for example, when the guide line 946 is parallel to a desired angled line 948.

Figure 19:
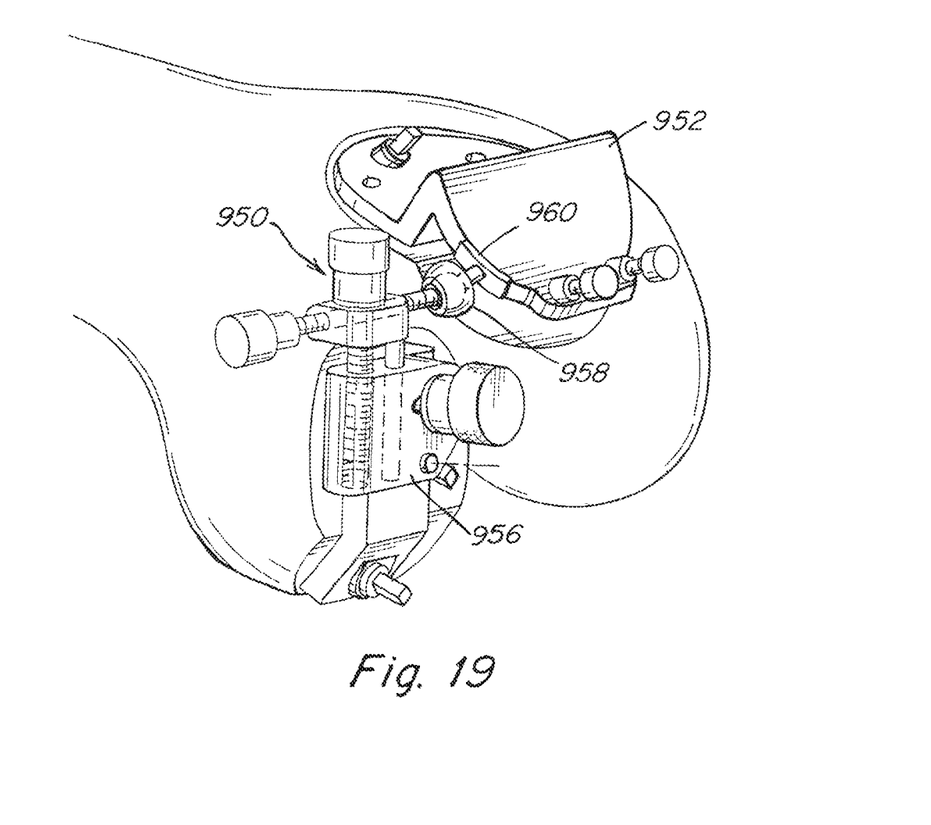
FIG. 19 is a perspective view of spacer arm to facilitate placement of a trochlear cutting guide.

FIG. 19 shows an arm guide to help with placement of a trochlear cutting guide according to some embodiments. After anterior resection is complete, the anterior cutting guide apparatus is removed, and an attachment 950 is attached to a rotating block 956 or other device attached to the femur. The attachment includes an arm 958 and a spacer guide 960 at an end of the arm to space a trochlear cutting guide such as a mill guide 952 a desired minimum distance from an expected medial femoral prosthesis. Once the arm is attached to the distal femoral resection surface, for example via rotating block 956, an end of the arm may be positioned to space a trochlear cutting guide at least a given distance from the distal femoral resection surface. The trochlear cutting guide may be place against spacer guide 960 (or other end piece of arm 958) or spaced an additional distance away from the spacer guide. In this manner, a trochlear component that is ultimately cemented to the femur during patellofemoral arthroplasty will not impinge or overlap the femoral prosthesis. In some embodiments, the rotation and the anterior/posterior height of the spacer guide 960 are adjustable. This adjustability allows selection of a minimum distance (e.g., 1 mm, 2 mm, or 3 mm) between the anticipated trochlear component and the expected femoral prosthesis. With the assistance of attachment 950, the trochlear preparation guide (such as mill guide) can be placed in a location which limits the risk of impingement or overlap the two femoral components. The arm guide of the present disclosure may be attached to devices disclosed herein, or attached to a separate device that is mounted to the femur.

In some embodiments, pre-operative scans may be used to facilitate aspects of a joint surgery, though embodiments disclosed herein may reduce or eliminate a need for such scans.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art. Accordingly, the foregoing description and drawings are by way of example only.

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

What is claimed is:

1. An apparatus for guiding an anterior distal femoral resection, the apparatus comprising:
a position block having a planar contact surface configured to be contacted to a distal femoral resection surface;
an anterior distal femoral cutting guide attached to the position block, the cutting guide having a cutting slot; and
a spacer arm configured to indicate a minimum distance at which to place a trochlear cutting guide relative to the apparatus;
wherein the spacer arm is attached to the position block via a rotating block which is attached to the position block.

2. An apparatus as in claim 1, wherein the spacer arm is adjustable in length.

3. An apparatus as in claim 1, further comprising a curved end piece positioned at an end of the spacer arm.

4. An apparatus as in claim 1, further comprising the trochlear cutting guide.

5. A method of spacing a trochlear cutting guide from a distal femoral resection surface on a medial condyle, the method comprising:
attaching an arm to a distal femoral resection surface on a medial condyle, wherein attaching an arm to a distal femoral resection surface comprises attaching the arm to a position block which is attached to the distal femoral resection surface;
directing an end of the arm toward an anterior distal femoral resection surface;
placing a trochlear cutting guide on an anterior distal femoral resection surface such that the trochlear cutting guide contacts the end of the arm or is spaced from the end of the arm.

6. A method as in claim 5, wherein attaching the arm to a position block which is attached to the distal femoral resection surface comprises attaching the arm to a rotating block which is attached to the position block.

* * * * *